US00PP31898P2

(12) United States Plant Patent
Ranney

(10) Patent No.: US PP31,898 P2
(45) Date of Patent: Jun. 23, 2020

(54) ***RHODODENDRON* PLANT NAMED 'NCRX2'**

(50) Latin Name: *Rhododendron hybrida*
Varietal Denomination: NCRX2

(71) Applicant: Thomas Green Ranney, Arden, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/501,351

(22) Filed: Mar. 28, 2019

(51) Int. Cl.
*A01H 5/02* (2018.01)
*A01H 6/36* (2018.01)

(52) U.S. Cl.
USPC ..... Plt./239
CPC ..... *A01H 6/364* (2018.05)

(58) Field of Classification Search
USPC ..... Plt./238, 239, 240
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct cultivar of *Rhododendron* plant named 'NCRX2' is disclosed, characterized by profuse pink/lavender flowers. Plants have a compact habit, and dark purple winter foliage. The new cultivar is a *Rhododendron*, suitable for ornamental garden purposes.

4 Drawing Sheets

Latin name of the genus and species: *Rhododendron hybrida.*
Variety denomination: 'NCRX2'.

BACKGROUND OF THE INVENTION

The present invention comprises a new and distinct triploid hybrid *Rhododendron* cultivar hereinafter referred to by the cultivar name 'NCRX2'. Developed by a breeding program in Mills River, N.C., 'NCRX2' was selected for a prolific floral display of pink-lavender flowers, compact form, reduced fertility, and showy, dark purple, winter foliage color. 'NCRX2' was selected from a population of sister plants derived from controlled, hand pollinations between the seed parent, *Rhododendron* 'Elite' (unpatented) and pollen parent, *Rhododendron* 'Bubblegum' (unpatented), in 2007.

The first asexual propagation of 'NCRX2' occurred in June 2009 by firm softwood cuttings at a research nursery in Mills River, N.C. 'NCRX2' roots readily from firm softwood cuttings treated with a basal dip of 5,000 ppm indole butyric acid (potassium salt) in water. 'NCRX2' has been found to retain its distinctive characteristics through successive asexual propagations over the course of 9 years.

SUMMARY OF THE INVENTION

The following are the unique combination of characteristics of this new cultivar when grown under standard horticultural practices at Mills River, N.C.

1. Profuse flowering with bright pink-lavender flowers.
2. Dark purple winter foliage.
3. Triploid cytotype.
4. Compact habit.

COMPARISON TO PARENT VARIETIES

'NCRX2' is similar in most horticultural characteristics to the seed parent. Plants of the new cultivar 'NCRX2' however differ in the following:

1. The new variety has pink/lavender flowers, while the seed parent has lavender/purple flowers.
2. The new variety is compact, while the seed parent is larger, less compact.

'NCRX2' is similar in most horticultural characteristics to the pollen parent. Plants of the new cultivar 'NCRX2' however differ in the following:

1. The new variety has pink/lavender flowers, while the pollen parent has brighter pink flowers.
2. The new variety is compact, while the pollen parent is larger, less compact.

COMMERCIAL COMPARISON

'NCRX2' can be compared to the commercial variety *Rhododendron* 'Amy Cotta', U.S. Plant Pat. No. 11,311. Plants of the new cultivar 'NCRX2' are similar to plants of 'Amy Cotta' in most horticultural characteristics. Plants of the new cultivar 'NCRX2', however, differ in the following:

1. The new variety has pink/lavender flowers, while this comparator has more purple flowers.
2. The new variety has dark purple Winter foliage, while this comparator has green Winter foliage.

BRIEF DESCRIPTION OF THE PHOTOGRAPHS

'NCRX2' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Rhododendron.*

DETAILED BOTANICAL DESCRIPTION

Figure 1:
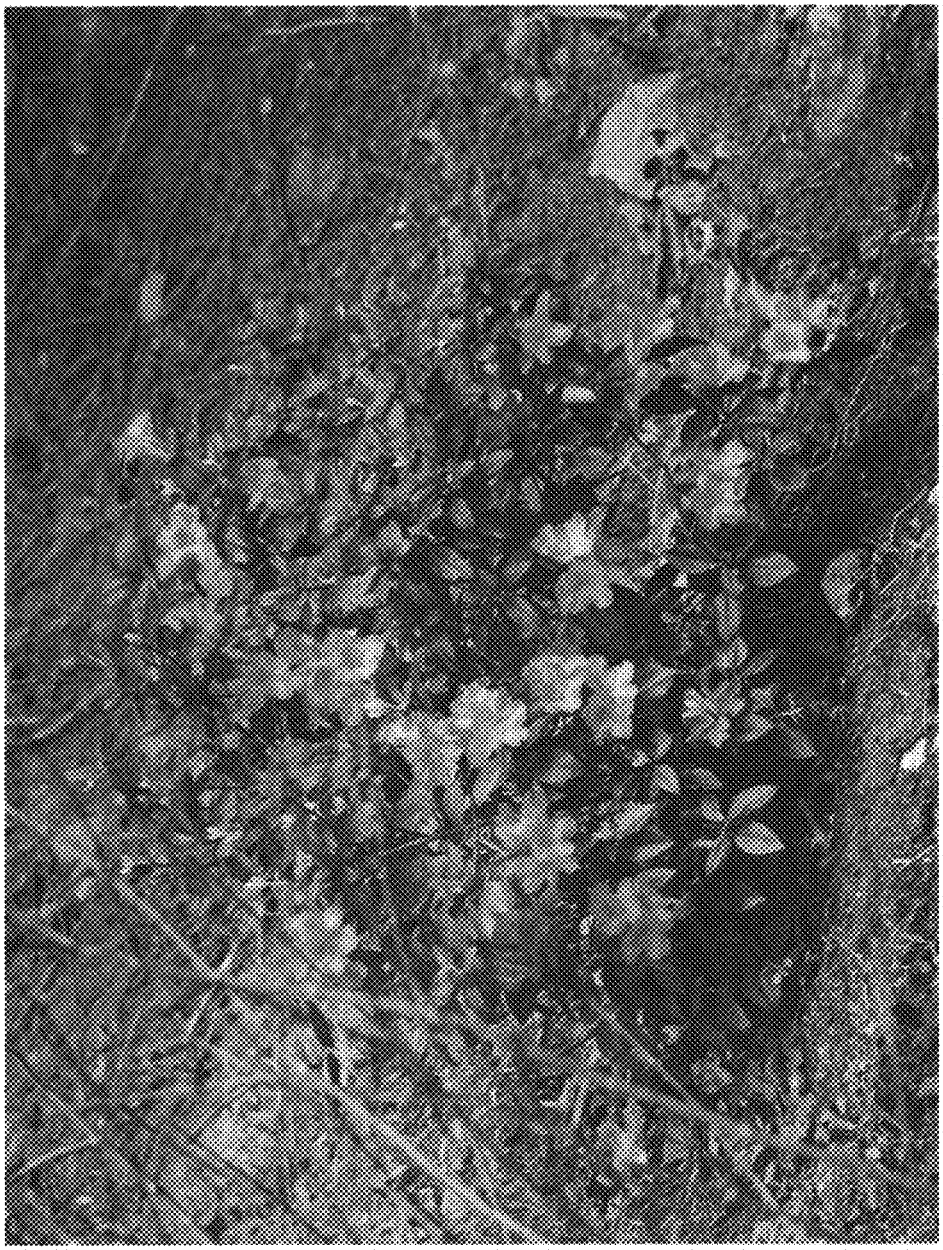
FIG. 1 shows the form and flowers of 4-year-old plant of 'NCRX2' growing in Arden, N.C. on Mar. 31, 2018.
Figure 2:
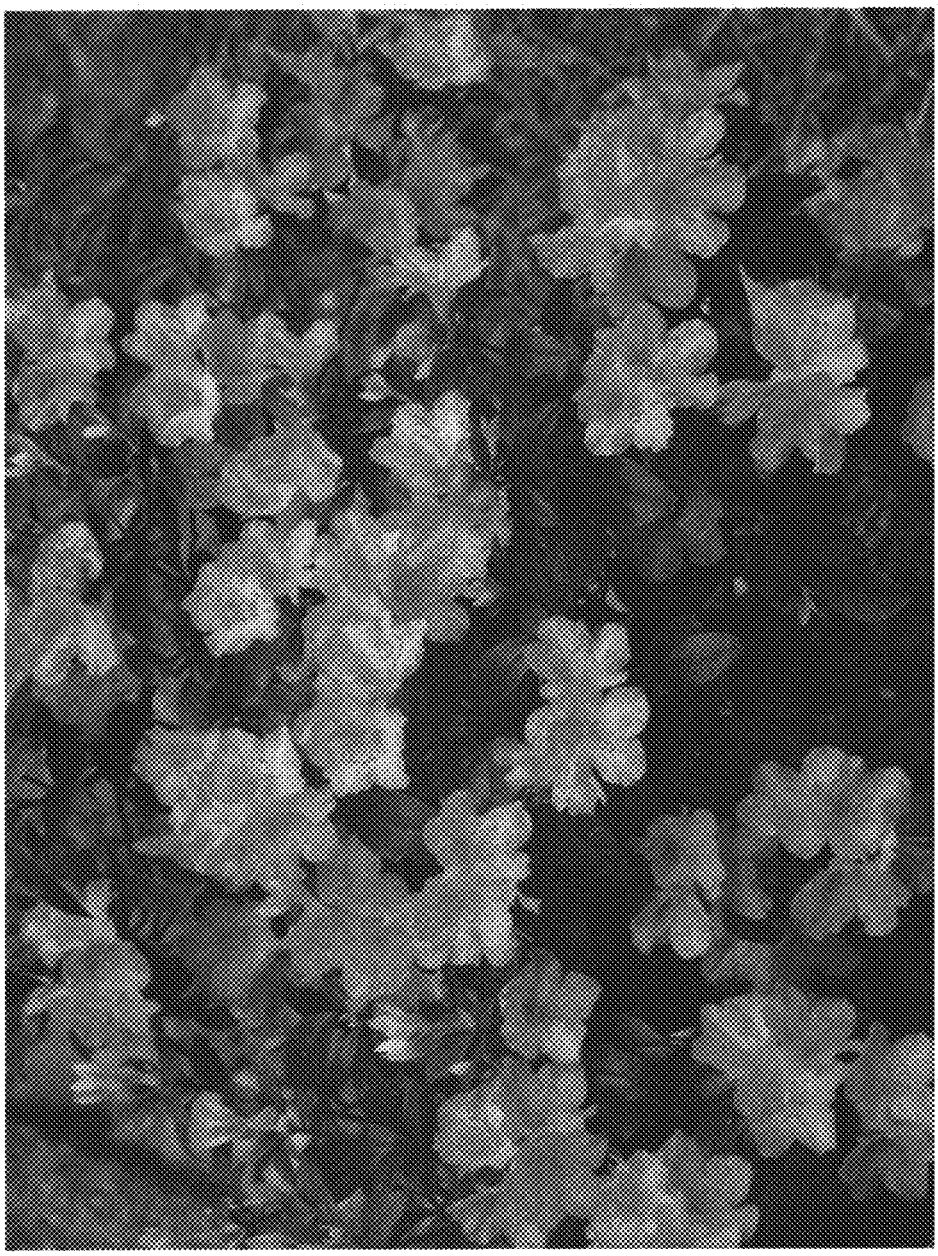
FIG. 2 shows the foliage and flowers of 4-year-old plant of 'NCRX2' growing in Arden, N.C. on Mar. 31, 2018.
Figure 3:
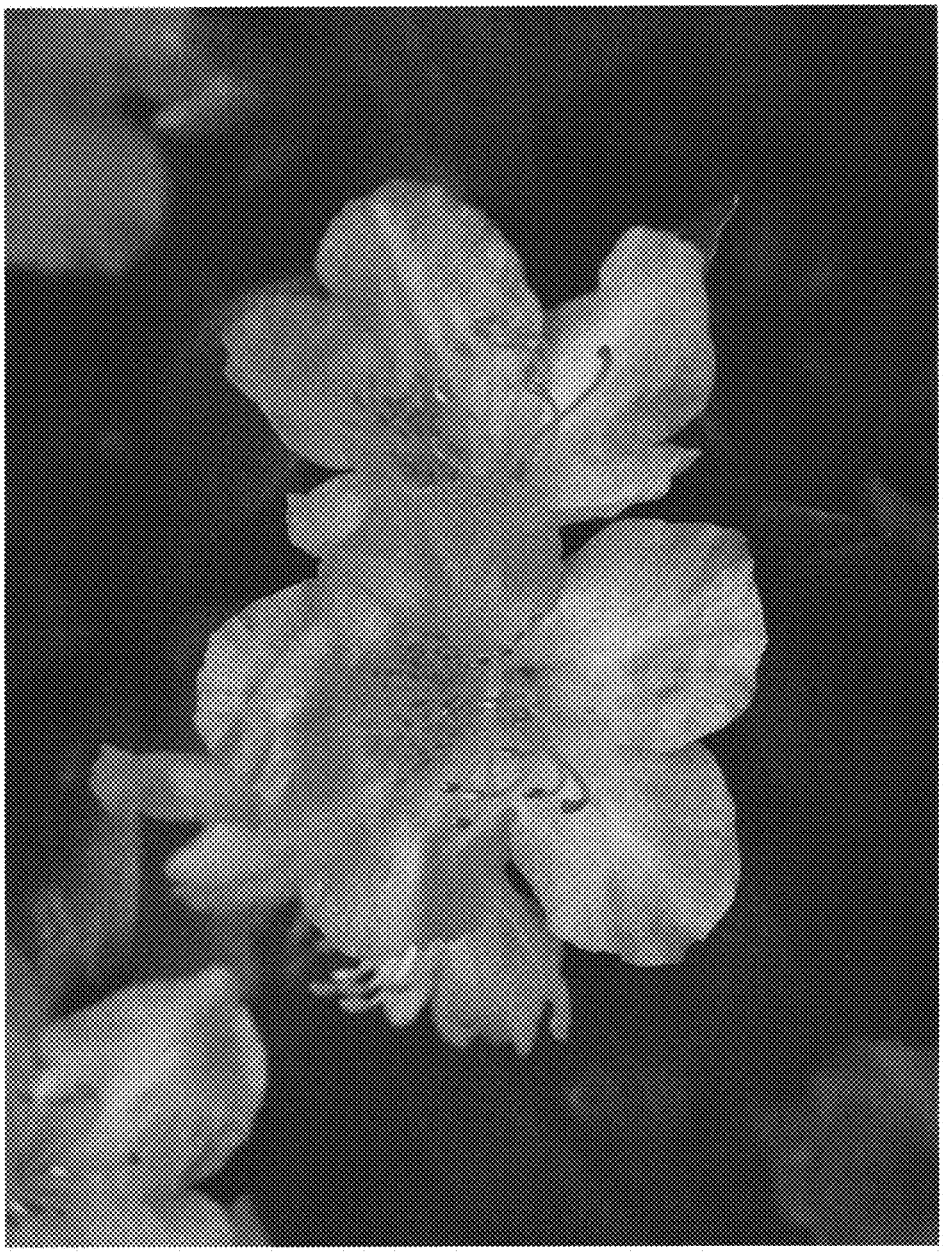
FIG. 3 shows a close up view of individual flowers of 4-year-old plant of 'NCRX2' growing in Arden, N.C. on Mar. 31, 2018.
Figure 4:
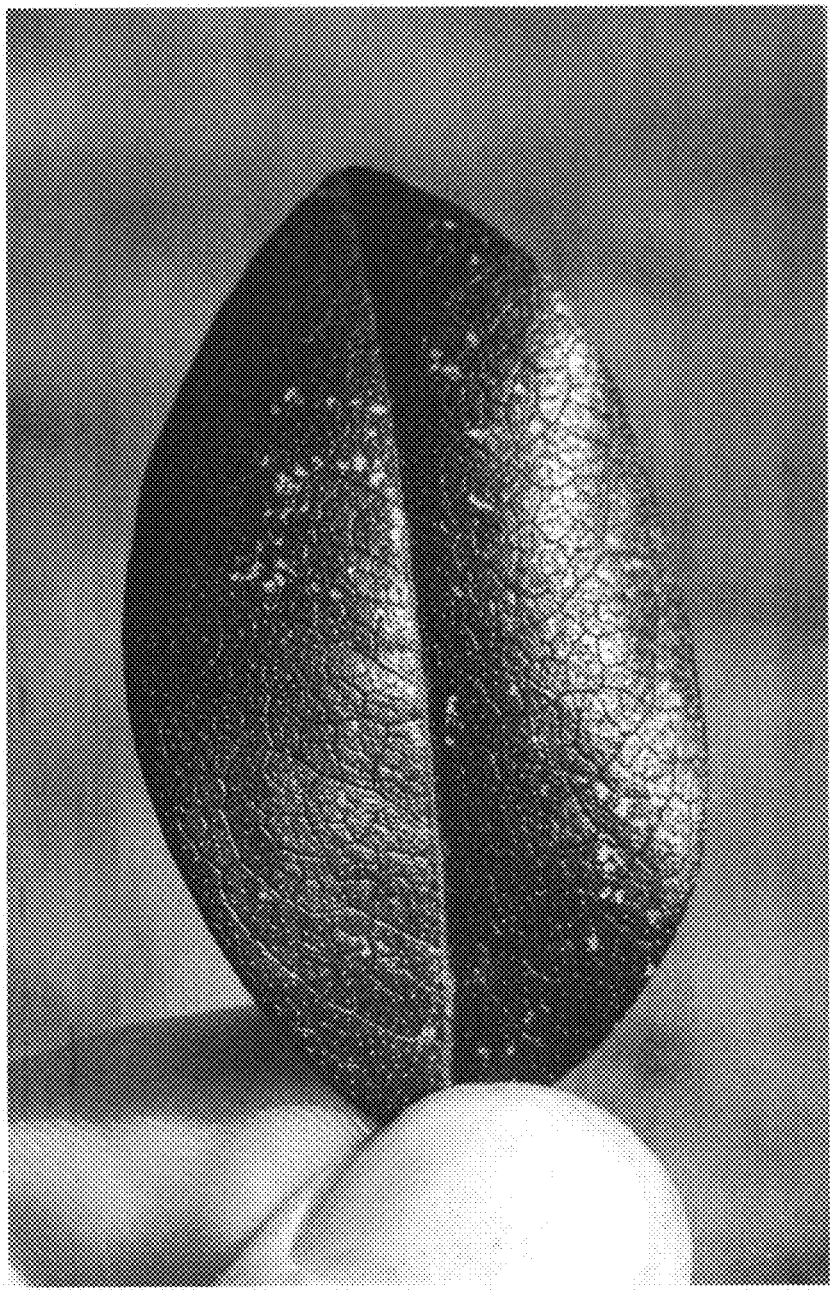
FIG. 4 shows the winter foliage color from 4-year-old plant of 'NCRX2' growing in Mills River, N.C. on Jan. 15, 2018.

The following is a detailed description of the botanical characteristics of the new and distinct hybrid *rhododendron* known by the denomination 'NCRX2'. The detailed description was taken of 4-year-old plants growing Mills River, N.C. For each measurable character, ten random measurements were recorded and used to derive averages and characteristic ranges. All colors cited herein refer to The Royal Horticultural Society Colour Chart (R.H.S.), 2015 Edition. Where specific dimensions, sizes, colors, and other characteristics are described, it is to be understood that these descriptions are approximations for variable characters that are labile and may change as a result of environment and growing conditions.

Botanical classification: *Rhododendron hybrida* 'NCRX2'.

Propagation: Typically by firm softwood cuttings.

PLANT

Plant type: Broad-leaf evergreen shrub.

Growth habit: Well-branched, rounded.

Height: 1 m.

Width: 1 m.

Growth rate: Moderate.

Roots: Fibrous.

Shoots (new growth):

- *Shape*.—Rounded.
- *Color*.—RHS Yellow-Green 144C which fades to Yellow-Green 144D at tips.
- *Texture*.—Glandular; older growth sees a reduction in visible glands.
- *Pubescence*.—Glabrous.
- *Shoot diameter*.—Average 2.2 mm.
- *Shoot length*.—Average 7.2 cm.
- *Stem aspect*.—Stems are held upright, often at a 45° angle from the branch.

Shoots (mature growth):

- *Shape*.—Rounded.
- *Color*.—Predominantly RHS Greyed-Orange 165B.
- *Texture*.—Smooth.
- *Pubescence*.—None.
- *Length*.—Average 17.1 cm.
- *Diameter*.—Average 2.0 mm.

Branching (mature growth):

- *Shape*.—Rounded.
- *Color*.—Between RHS Greyed-Orange 164B and 166A.
- *Texture*.—Smooth.
- *Pubescence*.—None.
- *Branch diameter*.—Average 5.0 mm.
- *Branch length*.—Average 28.6 cm.
- *Branching*.—Generally branches at terminal flowering points; branches arch upwards.
- *Branch aspect*.—Lower branches are held at approximately 90° angles; upper branches decrease in angle to approximately 45°.

Trunk (at soil line):

- *Shape*.—Round.
- *Color*.—Mix of RHS Grey-Brown N200B and RHS Greyed-Orange 177D. Exposed epidermis visible through exfoliation is often near Greyed-Orange 177D.
- *Texture*.—Exfoliates.
- *Pubescence*.—None.

Age of plant described: Approximately 4 years.

FOLIAGE

Leaf:

- *Type*.—Simple, lepidote.
- *Arrangement*.—Alternate.
- *Persistence*.—Evergreen to semi-evergreen.
- *Division*.—Entire.
- *Shape*.—Elliptic; occasionally ovate.
- *Orientation*.—Leaves are held approximately 45°-90° from the stem.
- *Aspect*.—Leaves are held flat, parallel to the ground.
- *Apex*.—Broadly acute; occasionally rounded or broadly acuminate, especially emerging leaves.
- *Base*.—Cuneate.
- *Margin*.—Entire.
- *Venation*.—Reticulate.
- *Color*.—Immature leaf, upper surface: Mix of RHS Yellow-Green 143A and Yellow-Green 144A.
- *Surface*.—Glabrous. Immature leaf lower surface: RHS Green 138B to Yellow-Green 145B.
- *Surface*.—Highly glandular.

Mature leaf:

- *Length*.—Average 6.6 cm.
- *Width*.—Average 3.5 cm.
- *Summer color*.—Upper surface: Near RHS Green NN137A.
- *Surface*.—Glabrous. Lower surface: Between RHS Yellow-Green 148A and 148B.
- *Surface*.—Glandular.
- *Fall/winter color*.—Upper surface: Variable, ranging from RHS Green NN137A, to Greyed-Purple N186C, 187A, 187B and 185A in some instances deepening into 186A. Lower surface: RHS Yellow-Green 152A.

Petiole:

- *Shape*.—Rounded with a flattened adaxial side.
- *Length*.—Average 10 mm.
- *Diameter*.—Average 1.3 mm.
- *Texture*.—Pubescent.
- *Color*.—Near RHS Greyed-Orange 177A.

FLOWER

Inflorescence:

- *Type*.—Congested terminal raceme (truss).
- *Fragrance*.—Very slight.
- *Inflorescence/truss measurements at anthesis*.—Length: Average 7.5 cm. Width: Average 10.8 cm.
- *Flowering season*.—Early to Mid-April (in Zone 6B).
- *Flower number and consistency*.—Plants flower each year consistently. Inflorescences are typically present on most primary terminal shoots.
- *Flowers per inflorescence*.—Variable, ranging from 3-12; lower branches often have fewer flowers.

*Longevity of flowers*.—Flowers persist for several weeks.

*Self-cleaning or persistent*.—Self-cleaning.

Flowers:

*Expanding buds*.—Shape: Obovate to elliptic. Length: Average 31.0 mm. Diameter (at widest point): Average 9.9 mm. Color: Varies between and includes RHS Red-Purple 72D and RHS Purple N74B. Bud scales: Present.

*Perianth* (*at anthesis*).—Depth: Average 4.0 cm. Width (at widest point): Average 4.9 cm. Height: Average 5.0 cm. Petal number: 5. Aspect: Individual flowers are held at near 90° angles at the base of the inflorescence; the angle decreases, and flowers are held more upright (towards 45° angles) along the peduncle towards the inflorescence apex. Shape: Elliptical, rounded petals fuse approximately at the halfway point and spread open resulting in a tubular, trumpet-like corolla; edges are slightly ruffled. Attachment: Pedicellate.

Petals:

*Length*.—Average 3.8 cm.

*Width*.—Average 21.6 mm.

*Petal shape*.—Elliptic.

*Apex*.—Rounded.

*Base*.—Fused.

*Margin*.—Entire.

*Fused or unfused*.—Fused.

*Color* (*at anthesis*).—Upper surface: RHS Red-Purple N74D to N74B. Surface: Glabrous. Blotch: RHS Red-Purple 71B and Red-Purple N66B. Length: Average 1.5 cm. Width: Average 1.6 cm. Lower surface: RHS Red-Purple N74D to N74B. Surface: Glabrous, with the presence of small white glands approximately 0.25 mm in diameter.

Calyx/receptacle:

*Shape*.—Lobed; sepals highly reduced.

*Arrangement*.—Whorled.

*Diameter*.—Average 3.8 mm.

*Depth*.—Average 2.19 mm.

*Apex*.—Broad acute.

*Margin*.—Entire.

*Surface*.—Glandular with fine, translucent pubescence at petal union.

*Sepal width*.—Average 2.3 mm.

*Sepal depth*.—Average 1.7 mm.

Peduncles:

*Shape*.—Rounded.

*Length*.—Average range about 3 to 5 cm from closest leaf.

*Diameter*.—Average 4 to 5 mm.

*Color*.—Near RHS Greyed-Orange 166B.

*Surface*.—Smooth.

Pedicels:

*Shape*.—Rounded.

*Length*.—Average 11.3 mm.

*Diameter*.—Average 1.1 mm.

*Color*.—RHS Red 48B mixed with Yellow-Green 145C. 145C coloration becomes more pronounced where the pedicel and peduncle meet.

*Surface*.—Highly glandular.

REPRODUCTIVE ORGANS

Gynoecium:

*Pistil number*.—1.

*Pistil length*.—Average 3.7 cm.

*Pistil diameter*.—Average 1.4 mm.

*Stigma shape*.—Flattened; ovoid.

*Stigma diameter*.—Average 1.2 mm.

*Style color*.—RHS Red-Purple 59A.

*Ovary diameter*.—Average 2.2 mm.

*Ovary length*.—Average 4.1 mm.

*Ovary color*.—RHS Green 139C.

Androecium:

*Stamen number*.—10.

*Anther shape*.—Ovoid with two apical pores.

*Anther attachment*.—Dorsifixed.

*Anther length*.—Average 2.0 mm.

*Anther width*.—Average 0.9 mm.

*Anther color*.—RHS Purple N77C.

*Filament length*.—Stamens are pentadynamous.

*Long stamens*.—Average 33.3 mm.

*Short stamens*.—Average 24.4 mm.

*Filament diameter*.—Average 0.4 mm.

*Filament color*.—Ranges between RHS Purple 75D and 75C, to Red-Purple 69D at base. Filaments are pubescent at base.

*Amount of pollen*.—Present, but very little produced.

*Pollen type*.—Threadlike, vicinate.

*Pollen color*.—RHS Purple 75C to 75D.

OTHER CHARACTERISTICS

Disease and pest resistance: Not observed to be susceptible nor resistant to normal diseases and pests of *Rhododendron*.

Temperature tolerance: Has been reliably cold hardy in USDA 6A.

Fruit/seed production: Not observed to date.

What is claimed is:

1. A new and distinct cultivar of *Rhododendron* plant named 'NCRX2' as herein illustrated and described.

* * * * *